(12) United States Patent
Martinez

(10) Patent No.: US 8,168,814 B2
(45) Date of Patent: May 1, 2012

(54) SYNTHESIS OF PHOSPHONIC ACID LABELED COMPOUNDS

(75) Inventor: Rodolfo A. Martinez, Santa Fe, NM (US)

(73) Assignee: New Mexico Highlands University, Las Vegas, NM (US)

( * ) Notice: Subject to any disclaimer, the term of this patent is extended or adjusted under 35 U.S.C. 154(b) by 320 days.

(21) Appl. No.: 12/421,458

(22) Filed: Apr. 9, 2009

(65) Prior Publication Data

US 2009/0259064 A1     Oct. 15, 2009

Related U.S. Application Data

(60) Provisional application No. 61/043,858, filed on Apr. 10, 2008.

(51) Int. Cl.
*C07F 9/02*     (2006.01)
(52) U.S. Cl. .................................... 558/184; 558/187
(58) Field of Classification Search ................ 558/184, 558/187
See application file for complete search history.

(56) References Cited

U.S. PATENT DOCUMENTS

| | | | | |
|---|---|---|---|---|
| 2,784,204 | A | 3/1957 | Heyna et al. | 260/397.6 |
| 6,221,335 | B1 * | 4/2001 | Foster | 424/1.81 |
| 6,603,008 | B1 * | 8/2003 | Ando et al. | 546/269.7 |
| 7,132,219 | B2 | 11/2006 | Sabnis et al. | 430/271.1 |
| 2006/0241057 | A1 | 10/2006 | Powers et al. | 514/18 |

OTHER PUBLICATIONS

Dyck et al., Journal of Neurochemistry, 1986, 46:399-404.*
Tonn et al., Biological Mass Spectrometry, 1993, 22:633-642.*
Haskins et al., 1982, Bionedical Mass Spectrometry, 7:269-277.*
Wolen et al., Journal of Clinical Pharmacology, 1986, 26:419-424,.*
Gouyette et al., Biomedical and Environmental Mass Spectrometry, 1988, 15:243-247.*
PCT—Notification of Transmittal of the International Search Report and the Written Opinion of the International Searching Authority, or the Declaration, Date of Mailing: Jun. 24, 2009.

* cited by examiner

*Primary Examiner* — Rei-tsang Shiao
(74) *Attorney, Agent, or Firm* — Melissa Asfahani; Luis M. Ortiz; Kermit D. Lopez

(57) ABSTRACT

High purity isotopically labeled phosphonic acid esters can be obtained from isotopically enriched Chloro[$^{13}$C]methyl phenyl sulfide The labeled phosphonic acid esters can then be used as precursors for the one step production of labeled vinyl sulfides, labeled vinyl sulfoxides, and labeled vinyl sulfones. The labeled phosphonic acid esters can also be reacted with a variety of aldehydes to produce extended vinyl systems that are isotopically labeled.

1 Claim, 8 Drawing Sheets

Benzene, [(1-[$^{13}$C]methyl[1,2-$^{13}$C$_2$]ethenyl)sulfonyl]

Benzene, [(1-[$^{13}$C]methyl[1,2-$^{13}$C$_2$]ethenyl)sulfinyl]

Benzene, [(1-[$^{13}$C]methyl[1,2-$^{13}$C$_2$]ethenyl)sulfide]

US 8,168,814 B2

SYNTHESIS OF PHOSPHONIC ACID LABELED COMPOUNDS

CROSS REFERENCE TO RELATED APPLICATIONS

This patent application claims the priority and benefit of U.S. Provisional Patent Application 61/043,858 filed Apr. 10, 2008 entitled "Synthesis of Phosphonic Acid Labeled Compounds" that is herein incorporated by reference.

TECHNICAL FIELD

The present invention relates to labeled compounds and more particularly to compounds that can be derived by way of a variety of schemes from isotopically enriched Chloro[$^{13}$C] methyl phenyl sulfide The labeled compounds include phosphonic acid esters that can subsequently be used to produce labeled vinyl sulfides, vinyl sulfoxides, vinyl sulfones, and extended vinyl systems.

BACKGROUND OF THE INVENTION

Phosphonates are extremely useful for the synthesis of other compounds such as the alkenes that can be obtained via the Homer-Wadsworth-Emmons reaction. Additionally, the use of stable isotopes has proven to be a promising analytical tool that has driven a need for isotopically labeled compounds. In order to meet the urgent and growing demand, high purity isotopically labeled compounds are needed.

BRIEF SUMMARY

The following summary is provided to facilitate an understanding of some of the innovative features unique to the embodiments and is not intended to be a full description. A full appreciation of the various aspects of the embodiments can be gained by taking the entire specification, claims, drawings, and abstract as a whole.

It is therefore an aspect of the embodiments to provide phosphonic acid esters. The phosphonic acid esters can be used as precursors for the one step production of vinyl sulfides, vinyl sulfoxides, and vinyl sulfones. The phosphonic acid esters can also be reacted with a variety of aldehydes to produce extended vinyl systems.

BRIEF DESCRIPTION OF THE DRAWINGS

The accompanying figures, in which like reference numerals refer to identical or functionally similar elements throughout the separate views and which are incorporated in and form a part of the specification, further illustrate aspects of the embodiments and, together with the background, brief summary, and detailed description serve to explain the principles of the embodiments.

DETAILED DESCRIPTION

Figure 1:
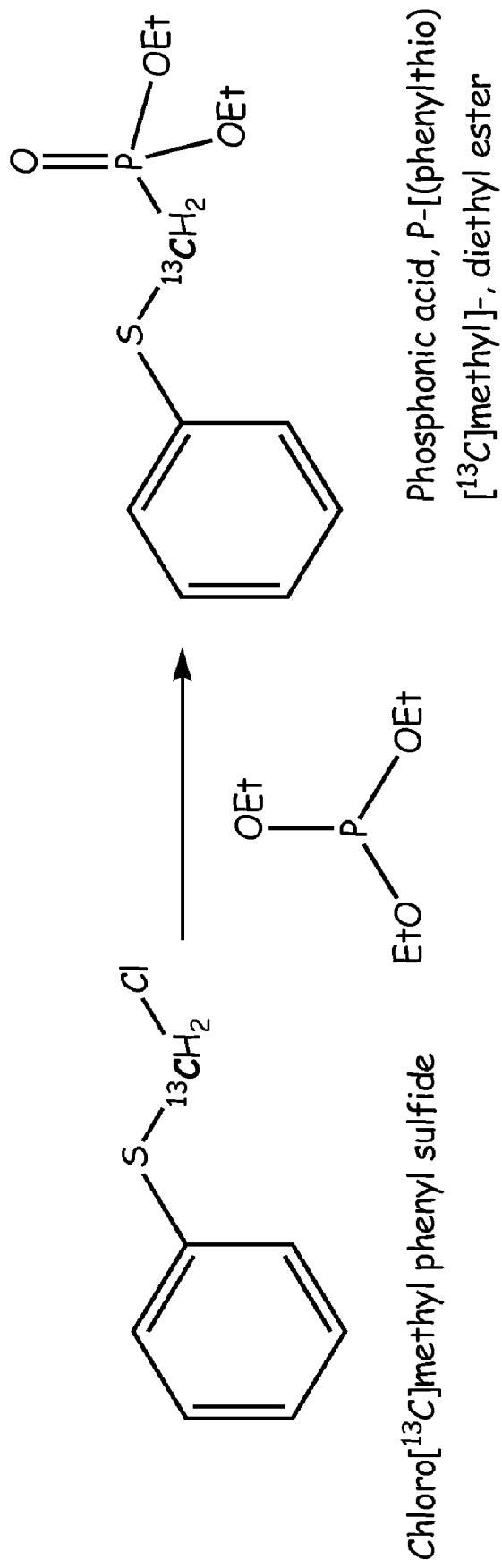
FIG. 1 illustrates obtaining Phosphonic acid, P-[(phenylthio) [$^{13}$C]methyl]-, diethyl ester in accordance with aspects of the embodiments.
Figure 2:
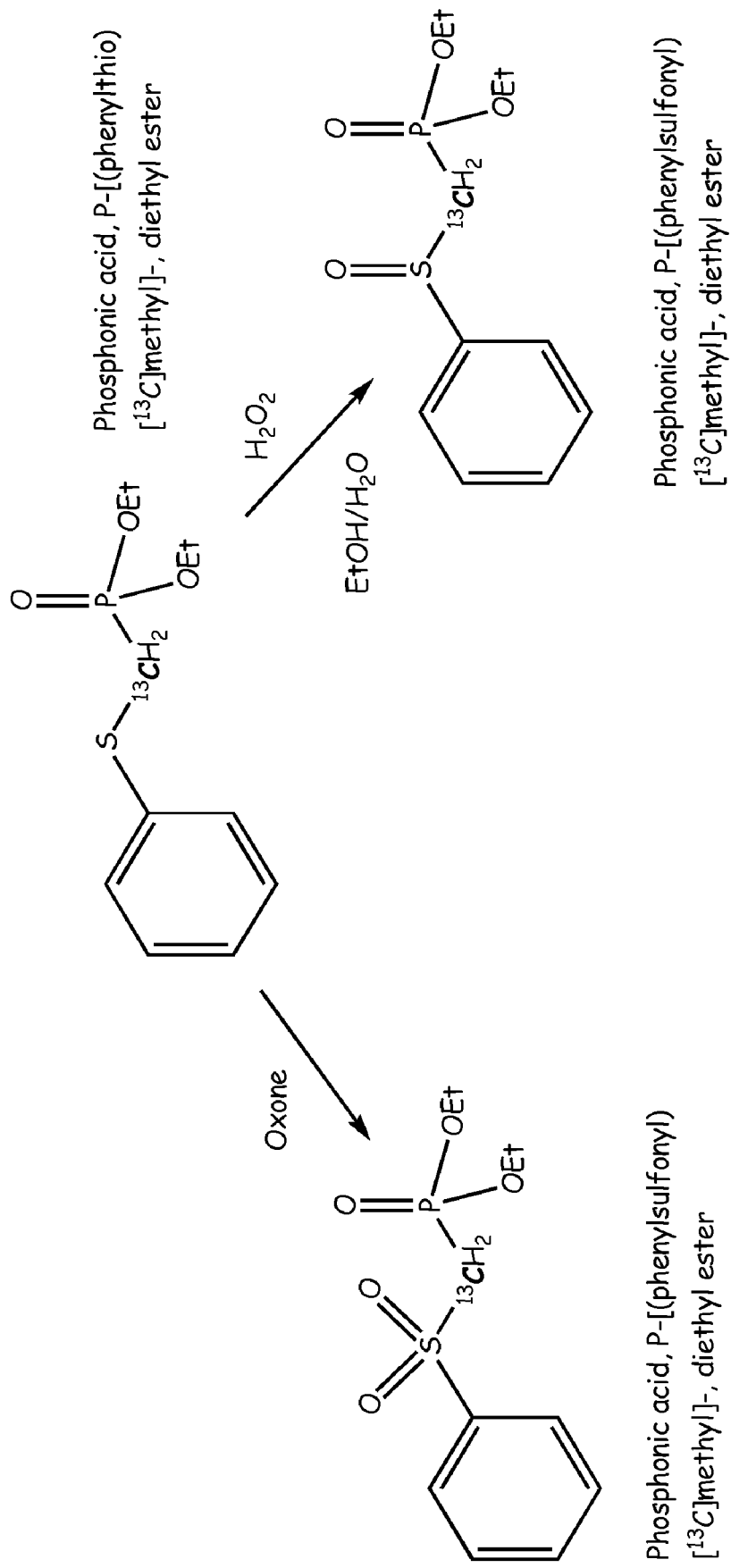
FIG. 2 illustrates obtaining Phosphonic acid, P-[(phenylsulfonyl) [$^{13}$C]methyl]-, diethyl ester and Phosphonic acid, P-[(phenylsulfinyl) [$^{13}$C]methyl]-, diethyl ester in accordance with aspects of the embodiments.
Figure 3:
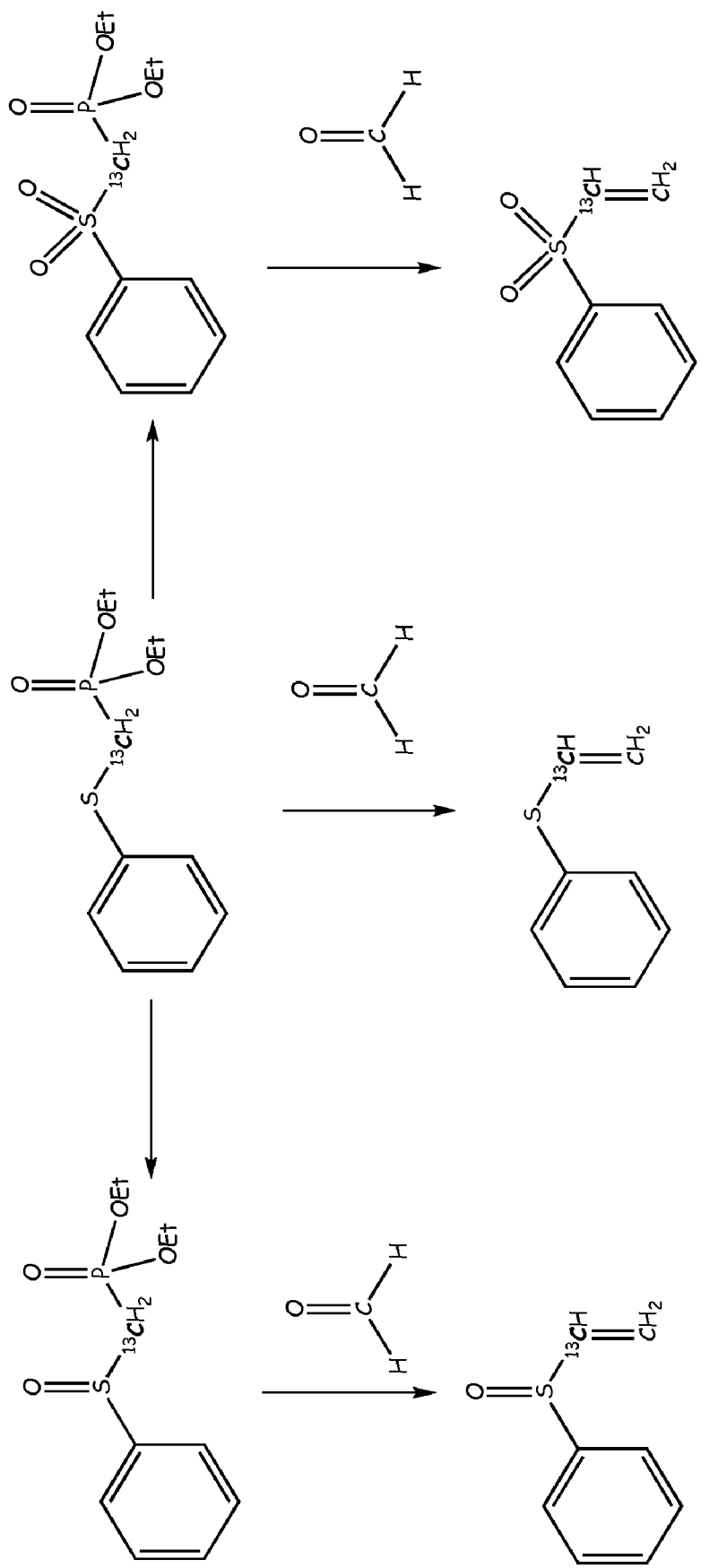
FIG. 3 illustrates obtaining labeled vinyl sulfides, labeled vinyl sulfoxides, and labeled vinyl sulfones in accordance with aspects of the embodiments.
Figure 4:
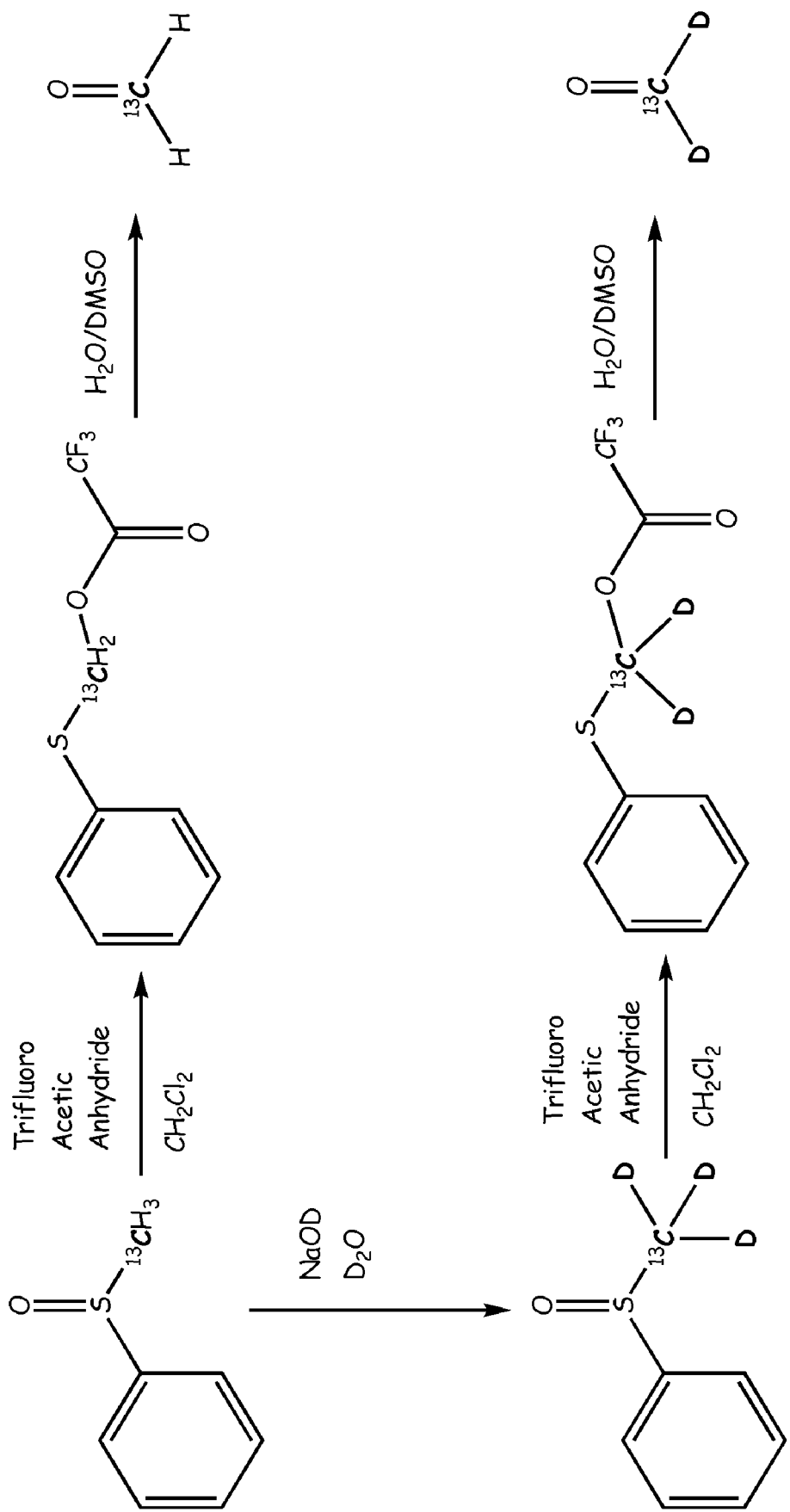
FIG. 4 illustrates obtaining labeled formaldehydes that can be reacted with labeled phosphonic acid esters in accordance with aspects of the embodiments.
Figure 5:
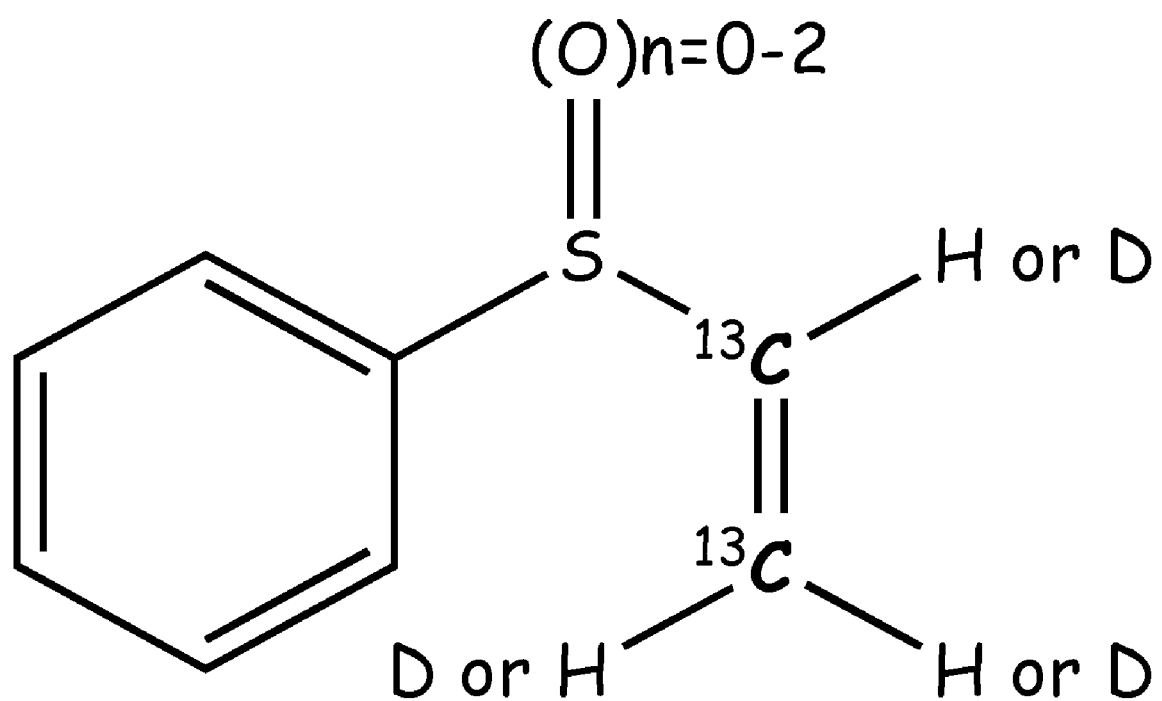
FIG. 5 illustrates a general structure for a vinyl system obtainable by combining the chemistry of FIG. 3 and FIG. 4 in accordance with aspects of the embodiments.
Figure 6:
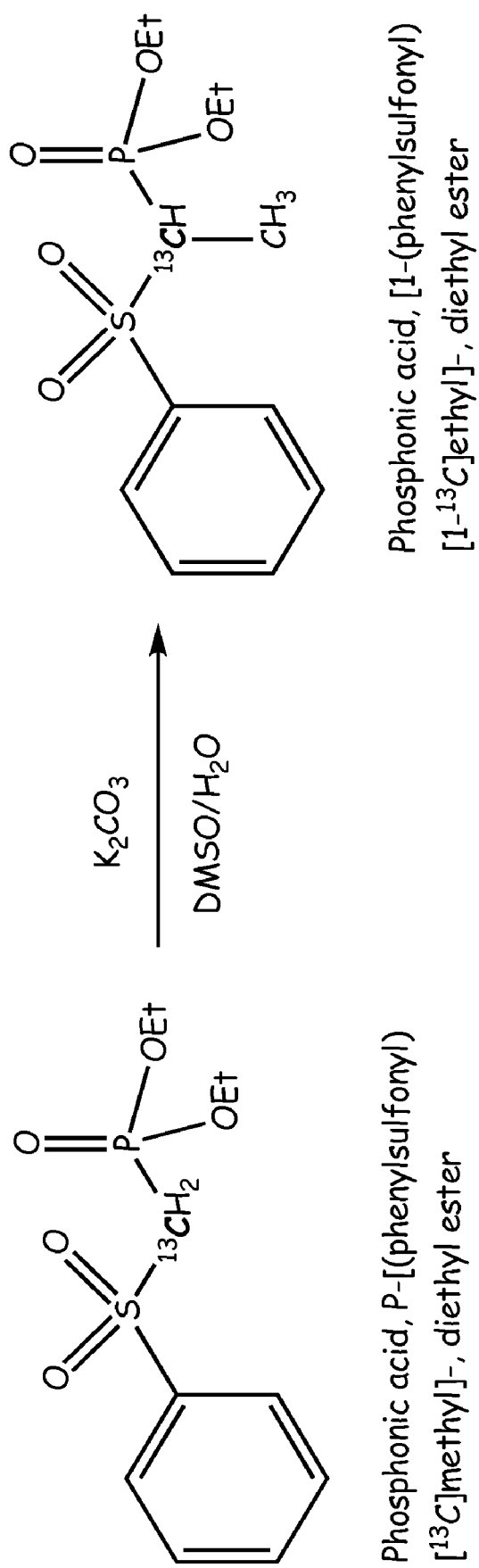
FIG. 6 illustrates obtaining labeled Phosphonic acid, [1-(phenylsulfonyl) [1-$^{13}$C]ethyl]-, diethyl ester from Phosphonic acid, P-[(phenylsulfonyl) [$^{13}$C]methyl]-, diethyl ester in accordance with aspects of the embodiments.
Figure 7:
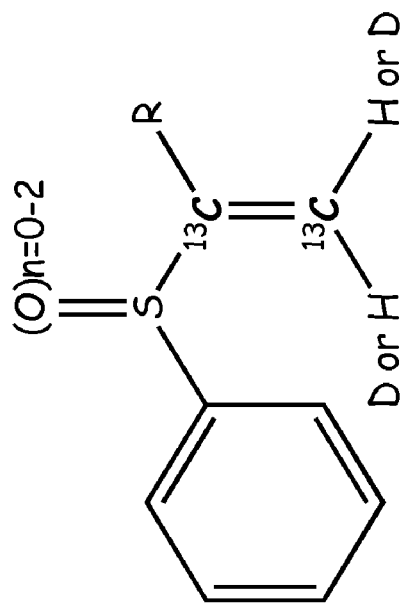
FIG. 7 illustrates additional labeled compounds obtainable by way of the scheme illustrated in FIG. 6 and in accordance with aspects of the embodiments.
Figure 7:
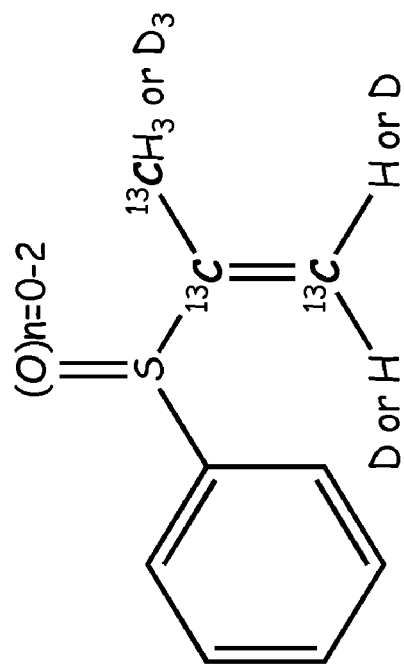
Figure 8:
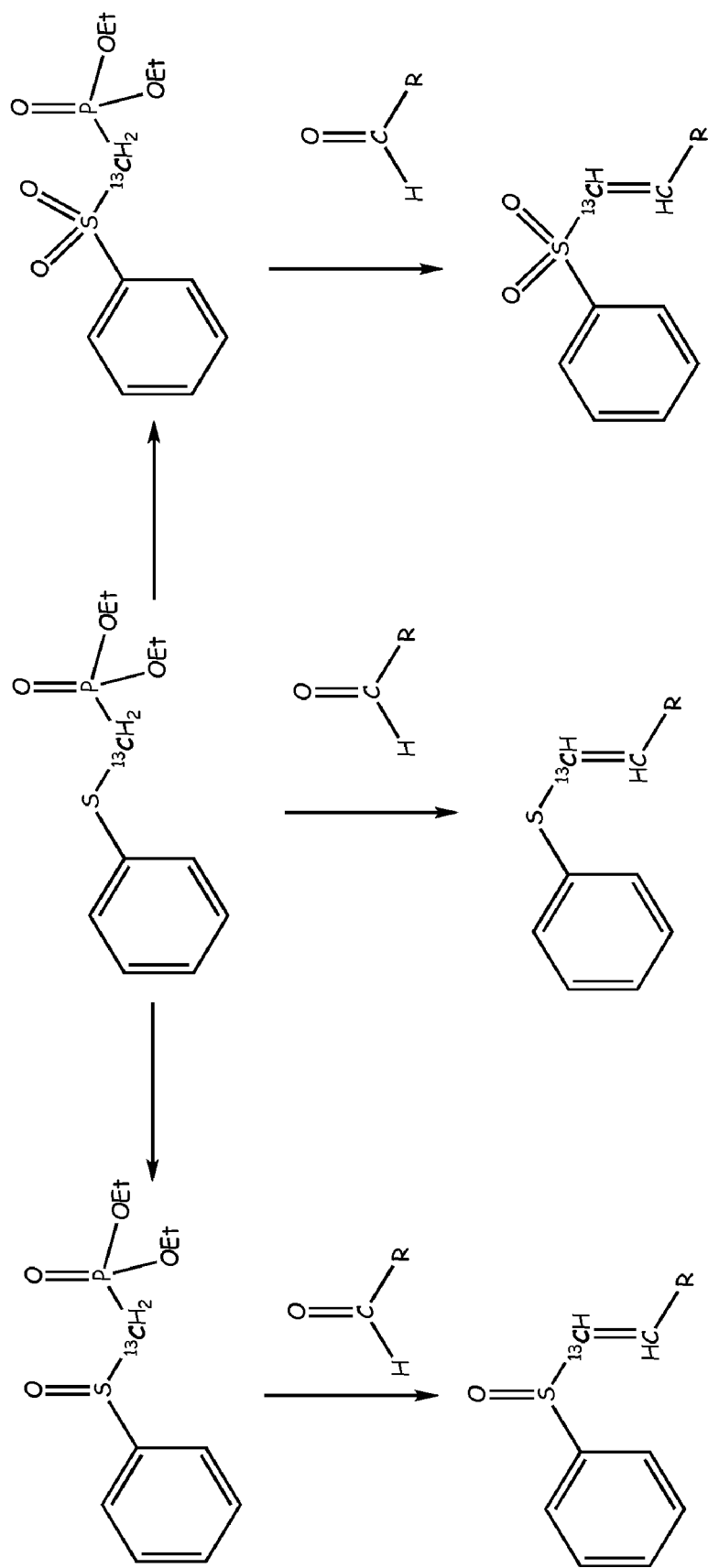
FIG. 8 illustrates obtaining isotopically labeled extended vinyl systems in accordance with aspects of the embodiments.

The following description contains a series of examples wherein previously known labeled compounds are processed to yield highly pure labeled compounds that are not previously known.

High purity isotopically labeled phosphonic acid esters can be obtained from isotopically enriched Chloro[$^{13}$C]methyl phenyl sulfide The labeled phosphonic acid esters can then be used as precursors for the one step production of labeled vinyl sulfides, labeled vinyl sulfoxides, and labeled vinyl sulfones. The labeled phosphonic acid esters can also be reacted with a variety of aldehydes to produce extended vinyl systems that are isotopically labeled.

Synthesis of Phosphonic acid, P-[(phenylthio) [$^{13}$C]methyl]-, diethyl ester

Chloro [$^{13}$C]methyl phenylsulfide (9.0 g, 56.4 mmol, 1.0 equivalent) was dissolved in triethyl phosphite (15 mL, 84.7 mmol, 1.5 eq) in a 500 mL Morton Flask fitted with a reflux condenser. The homogeneous reaction mixture was stirred and heated to 130° C. (internal temperature). After 5 hours of refluxing, the reaction was found to be complete by $^{13}$C NMR by taking an aliquot from the reaction mixture, dissolving it into CDCl$_3$, and monitoring the disappearance of chloro [$^{13}$C] methyl phenylsulfide (δ=51.2 ppm) and subsequent appearance of the desired diethyl phenylthio [$^{13}$C]methyl phosphonate (δ=27.6, 29.6 ppm). The reaction mixture was subjected to reduced pressure (3 mm) to remove excess triethyl phosphite through a short path distillation apparatus using a liquid nitrogen trap. The resulting colorless liquid (14.72 g, 99.9%), was used without further purification.

The spectra data are as follows:

$^1$H NMR (CDCl$_3$, 300 MHz): δ=1.3 (t, 6H, J=6.94 Hz), 2.97, 3.43 (dd, 2H, J=138.40 Hz 4.14 (m, 4H), 7.20-7.45 (m, 5H$_{arom}$).

$^{13}$C NMR (CDCl$_3$, 75 MHz): δ=16.48, 16.56 (d, J=6.12 Hz, OCH$_2$), 27.67, 29.64 (d, J=148.41 Hz, $^{13}$CH$_2$), 62.83, 62.92 (d, J=6.59 Hz, CH$_3$), 126.95, 129.15, 129.74, 135.7 (C$_{arom}$).

Synthesis of Phosphonic acid, P-[(phenylsulfinyl) [$^{13}$C]methyl]-, diethyl ester Diethyl phenylthio-[$^{13}$C]-methyl phosphonate (6.28 g, 24.0 mmol, 1.0 eq) was dissolved in two-hundred proof ethanol (60 mL) in a 500 mL Morton flask. Solution was then cooled using an ice-water bath while stirred before it was added an aqueous solution of hydrogen peroxide (30 wt. % in $H_2O$, 24.6 mL, 240.5 mmol, 10.0 eq). Upon addition of the aqueous hydrogen peroxide solution the reaction appeared homogeneous and the reaction mixture was permitted to warm to room temperature slowly as the ice bath melted. The Morton flask was kept in the dark by covering with aluminum foil and keeping hood lights off. After 4 days, the reaction was found to be complete by $^{13}C$ NMR by taking an aliquot from the reaction mixture, dissolving it into $CDCl_3$, and monitoring the disappearance of diethyl phenylthio-[$^{13}C$]-methyl phosphonate ($\delta$=25 and 27 ppm) and subsequent appearance of the desired diethyl phenylsulfinyl-[$^{13}C$]-methyl phosphonate ($\delta$=50 and 52 ppm). The reaction mixture was then worked up by adding dichloromethane (80 mL) and stirring while flask was submerged in an ice-bath. Slowly, sodium bisulfite was added until no more oxidant was seen using KI starch paper. Organic layer was partitioned out and washed with more water (15 mL, 2×). Organic layer was then dried over sodium sulfate, filtered, and evaporated via vacuum using a rotary evaporator to yield a clear liquid (6.29 g, 94%) which was used without further purification.

The spectra data are as follows:
$^1H$ NMR ($CDCl_3$, 300 MHz): $\delta$=1.3 (t, 6H, J=6.73 Hz), 3.54, 4.0 (dd, 2H, J=133.35 Hz), 4.16 (m, 4H), 7.44-8.12 (m, 5$H_{arom}$).

Synthesis of Phosphonic acid, P-[(phenylsulfonyl) [$^{13}C$]methyl]-, diethyl ester Diethyl phenylthio [$^{13}C$]methyl phosphonate (5.7 g, 21.8 mmol, 1.0 eq) was dissolved in a 50/50 mixture of ethyl acetate (30 mL) and ethanol (30 mL) in a 500 mL Morton flask. Solution was then cooled using an ice-water bath while stirred before it was added an aqueous solution (95 mL) of oxone (40.23 g, 65.4 mmol, 3.0 eq). Upon addition of the aqueous oxone solution the reaction appeared heterogeneous and the reaction mixture was permitted to warm to room temperature slowly as the ice bath melted. After 30 minutes, the reaction was found to be complete by $^{13}C$ NMR by taking an aliquot from the reaction mixture, dissolving it into $CDCl_3$, and monitoring the disappearance of diethyl phenylthio [$^{13}C$]methyl phosphonate ($\delta$=26.4 and 28.4 ppm) and subsequent appearance of the desired diethyl phenylsulfonyl [$^{13}C$]methyl phosphonate ($\delta$=50.5 and 52.3 ppm). The reaction mixture was then worked up by adding dichloromethane (100 mL) to help precipitate the oxone, stirred, and then filtered. Filtrate organic layer was partitioned out and washed with more water (20 mL, 4×) until no more oxidant was seen via KI starch paper. Solids were again suspended over dichloromethane (50 mL) and stirred before they were filtered. Resulting filtrate was added water (20 mL) and organic layer was partitioned out and washed with more water (20 mL, 4×) to remove oxidant. Organic layers from both extractions were then combined and dried over sodium sulfate, filtered, and evaporated via vacuum using a rotary evaporator to yield a white solid (6.38 g, 99.9%) which was used without further purification.

The spectra data are as follows:
$^1H$ NMR ($CDCl_3$, 300 MHz): $\delta$=1.3 (t, 6H, J=6.73 Hz), 3.54, 4.0 (dd, 2H, J=133.25 Hz), 4.16 (m, 4H), 7.44-8.12 (m, 5$H_{arom}$).
$^{13}C$ NMR ($CDCl_3$, 75 MHz): $\delta$=16.3, 16.4 (d, J=6.13 Hz, $OCH_2$), 53.11, 54.93 (d, J=137.79 Hz, $^{13}CH_2$), 63.58, 63.67 (d, J=6.32 Hz, $CH_3$), 128.51, 129.28, 134.20, 137.0 ($_{arom}$).

Synthesis of Phenyl-1-methyl [1-$^{13}C$]vinyl sulfone

Diethyl phenylsulfonyl-[1-$^{13}C$]-methyl-1-methyl phosphonate (1.17 g, 3.8 mmol, 1.0 equivalent) that had not been isolated was in DMSO (20 mL) and $H_2O$ (10 mL) in a 250 mL Morton Flask. The heterogeneous mixture also had $K_2CO_3$ (2.8 g, 19.9 mmol, 3.0 eq). Aqueous formaldehyde solution (37 wt./wt. %, 0.281 mL, 3.8 mmol, 1.0 eq) was added while the reaction mixture was stirring. One and a half hours after aldehyde addition the reaction was found to be complete by $^{13}C$ NMR by taking an aliquot from the reaction mixture and monitoring the disappearance of diethyl phenylsulfonyl-[1-$^{13}C$]-methyl-1-methyl phosphonate ($\delta$=55, 57 ppm) and subsequent appearance of the desired phenyl-[1-$^{13}C$]-1-methyl vinyl sulfone ($\delta$=145 ppm). The reaction mixture was then worked up by adding dichloromethane (30 mL) and organic layer was partitioned out and washed with more water (10 mL, 2×). Organic layer was then dried over sodium sulfate, filtered, and evaporated via vacuum using a rotary evaporator to yield a clear liquid (579.8 mg). Crude product was then purified via dry column chromatography using a 20:80 ethyl acetate:hexane eluant to give a colorless liquid (295.7 mg, 51%) which was used without further purification.

The spectra data are as follows:
$^1H$ NMR ($CDCl_3$, 300 MHz): $\delta$=5.97-6.11 (m, 1H, J=9.29 Hz), 6.32-6.51 (m, 1H), 6.32-7.01 (m, 1H), 7.53-7.92 (m, 5$H_{arom}$).
$^{13}C$ NMR ($CDCl_3$, 75 MHz): $\delta$=127.45 ($CH_2$), 128.00, 129.49, 133.82, 139.57 ($C_{arom}$), 138.53 ($^{13}CH$).

Synthesis of i-Phenylsulfinyl-1-[1-$^{13}C$]propene

Diethyl phenylsulfinyl [$^{13}C$]methyl phosphonate (464.3 mg, 1.7 mmol, 1.0 equivalent) was dissolved in DMSO (2.5 mL) and $H_2O$ (1 mL) in a 100 mL Morton Flask. The homogeneous mixture was stirred and cooled in an ice-bath at 0° C. An aqueous (1.5 mL) solution of $K_2CO_3$ (708.8 mg, 5.0 mmol, 3.0 eq) was then added slowly to the reaction mixture to enable anion formation. After 10 minutes of stirring, acetaldehyde (0.12 mL, 2.2 mmol, 1.3 eq) was added, turning solution cloudy, before the heterogeneous reaction mixture was removed from the ice bath and allowed to reach room temperature. Five days after aldehyde addition the reaction was found to be mostly complete by $^{13}C$ NMR by taking an aliquot from the reaction mixture and monitoring the disappearance of diethyl phenylsulfinyl [$^{13}C$]methyl phosphonate ($\delta$=50, 52 ppm) and subsequent appearance of the desired 1-phenylsulfinyl-1-[1-$^{13}C$]propene ($\delta$=134 ppm). A little starting material remained, however, two other by-product peaks at 53 and 55 ppm were now of greater intensity. The reaction mixture was then worked up by adding dichloromethane (20 mL) and organic layer was partitioned out and washed with more water (5 mL, 2×). Organic layer was then dried over sodium sulfate, filtered, and evaporated via vacuum using a rotary evaporator to yield a yellow liquid (205.6 mg). Crude product was then purified via dry column chromatography using a 70:30 ethyl acetate:hexane eluant to give a colorless liquid (49.7 mg, 25.4%) which was used without further purification.

The spectra data are as follows:
$^1H$ NMR ($CDCl_3$, 300 MHz): $\delta$=1.88-1.93 (m, 3H), 5.97 (dq, 0.5H, J=15.14 Hz), 6.50-6.68 (m, 1.5H), 7.42-7.95 (m, 5$H_{arom}$).
$^{13}C$ NMR ($CDCl_3$, 75 MHz): $\delta$=17.93 ($CH_3$), 124.49, 124.50 (d, J=1.10 Hz, CH), 129.38, 130.93, 136.55, 144.24 ($C_{arom}$), 136.41 ($^{13}CH$).

Synthesis of 1-Phenylsulfonyl-1-[1-$^{13}C$]propene

Diethyl phenylsulfonyl [$^{13}C$]methyl phosphonate (560.4 mg, 1.9 mmol, 1.0 equivalent) was dissolved in DMSO (3.0 mL) and H$_2$O (1.5 mL) in a 100 mL Morton Flask. The homogeneous mixture was stirred and cooled in an ice-bath at 0° C. An aqueous (1.5 mL) solution of K$_2$CO$_3$ (808.8 mg, 5.7 mmol, 3.0 eq) was then added slowly to the reaction mixture to enable anion formation. After 10 minutes of stirring, acetaldehyde (0.17 mL, 3.1 mmol, 1.6 eq) was added before the heterogeneous reaction mixture was removed from the ice bath and allowed to reach room temperature. One hour after aldehyde addition the reaction was found to be complete by $^{13}$C NMR by taking an aliquot from the reaction mixture and monitoring the disappearance of diethyl phenylsulfonyl [$^{13}$C] methyl phosphonate ($\delta$=50, 52 ppm) and subsequent appearance of the desired 1-phenylsulfonyl-1-[1-$^{13}$C]propene ($\delta$=130 ppm). The reaction mixture was then worked up by adding dichloromethane (20 mL) and organic layer was partitioned out and washed with more water (5 mL, 2×). Organic layer was then dried over sodium sulfate, filtered, and evaporated via vacuum using a rotary evaporator to yield a yellow solid (271.4 mg). Crude product was then purified via dry column chromatography using a 30:70 ethyl acetate:hexane eluant to give a white solid (125.9 mg, 46.4%) which was used without further purification.

The spectra data are as follows:
$^1$H NMR (CDCl$_3$, 300 MHz): $\delta$=1.91 (dt, 3H, J=7.11 Hz), 6.04-6.20 (m, 0.5H), 6.60-6.70 (m, 0.5H), 6.91-7.04 (m, 1H), 7.46-7.96 (m, 5H$_{arom}$).
$^{13}$C NMR (CDCl$_3$, 75 MHz): $\delta$=17.23, 17.24 (d, J=1.03 Hz, CH$_3$), 127.42 (CH), 129.21, 131.15, 133.25, 142.12 (C$_{arom}$), 131.67 ($^{13}$CH).

Synthesis of 2-Phenylsulfonyl-1-[2-$^{13}$C]propene

Diethyl phenylsulfonyl [1-$^{13}$C]methyl-1-methyl phosphonate (1.17 g, 3.8 mmol, 1.0 equivalent) that had not been isolated was in DMSO (10 mL) and H$_2$O (10 mL) in a 250 mL Morton Flask. The heterogeneous mixture also had K$_2$CO$_3$ (1.57 g, 11.4 mmol, 3.0 eq). Aqueous formaldehyde solution (37 wt./wt. %, 0.281 mL, 3.8 mmol, 1.0 eq) was added while the reaction mixture was stirring. One and a half hours after aldehyde addition the reaction was found to be complete by $^{13}$C NMR by taking an aliquot from the reaction mixture and monitoring the disappearance of diethyl phenylsulfonyl [1-$^{13}$C]methyl-1-methyl phosphonate ($\delta$=55, 57 ppm) and subsequent appearance of the desired 2-phenylsulfonyl-1-[2-$^{13}$C]propene ($\delta$=145 ppm). The reaction mixture was then worked up by adding dichloromethane (30 mL) and organic layer was partitioned out and washed with more water (10 mL, 2×). Organic layer was then dried over sodium sulfate, filtered, and evaporated via vacuum using a rotary evaporator to yield a clear liquid (579.8 mg). Crude product was then purified via dry column chromatography using a 20:80 ethyl acetate:hexane eluant to give a colorless liquid (295.7 mg, 51%) which was used without further purification.

The spectra data are as follows:
$^1$H NMR (CDCl$_3$, 300 MHz): $\delta$=1.95 (m, 3H, J=6.92 Hz), 5.73 (m, 1H, J=1.49 Hz), 6.27 (m, 1H, J=4.46 Hz), 7.52-7.96 (m, 5H$_{arom}$).
$^{13}$C NMR (CDCl$_3$, 75 MHz): $\delta$=16.03, 16.62 (d, J=44.49 Hz, CH$_3$), 128.23 (CH$_2$), 123.82, 124.79, 129.25, 133.61 (C$_{arom}$), 146.17 ($^{13}$CH).

Synthesis of Phenylsulfinyl [$^{13}$C]methane

Phenylthio [$^{13}$C]methane (8.0 g, 63.9 mmol, 1.0 eq) was dissolved in two-hundred proof ethanol (80 mL) in a 250 mL Morton flask. Solution was then cooled using an ice-water bath while stirred before it was added an aqueous solution of hydrogen peroxide (30 wt. % in H$_2$O, 7.83 mL, 76.7 mmol, 1.2 eq). Upon addition of the aqueous hydrogen peroxide solution the reaction appeared homogeneous and the reaction mixture was permitted to warm to room temperature slowly as the ice bath melted. The Morton flask was kept in the dark by covering with aluminum foil and keeping hood lights off. After 15 days, the reaction was found to be complete by $^{13}$C NMR by taking an aliquot from the reaction mixture and monitoring the disappearance of phenylthio [$^{13}$C]methane ($\delta$=16 ppm) and subsequent appearance of the desired phenylsulfinyl [$^{13}$C]methane ($\delta$=44 ppm). The reaction mixture was then worked up by adding dichloromethane (100 mL) and stirring while flask was submerged in an ice-bath. Slowly, sodium bisulfite was added until no more oxidant was seen using KI starch paper. Organic layer was partitioned out and washed with more water (20 mL, 2×). Organic layer was then dried over sodium sulfate, filtered, and evaporated via vacuum using a rotary evaporator to yield a clear liquid (8.19 g, 91%) which was used without further purification.

The spectra data are as follows:
$^1$H NMR (CDCl$_3$, 300 MHz): $\delta$=2.73 (d, 3H, J=138.96 Hz), 7.45-7.97 (m, 5H$_{arom}$).
$^{13}$C NMR (CDCl$_3$, 75 MHz): $\delta$44.14 ($^{13}$CH$_3$), 123.63, 123.65 (d, J=1.14 Hz, C$_{arom}$), 129.51, 131.18, 145.91 (C$_{arom}$).
$^{13}$C NMR (CDCl$_3$, 75 MHz): $\delta$=16.3, 16.4 (d, J=6.13 Hz, OCH$_2$), 53.11, 54.93 (d, J=137.79 Hz, $^{13}$CH$_2$), 63.58, 63.67 (d, J=6.32 Hz, CH$_3$), 128.51, 129.28, 134.20, 137.0 (C$_{arom}$).

Synthesis of Phenyl [1,2-$^{13}$C$_2$]vinyl sulfone

Phenylsulfinyl [$^{13}$C]methane (0.481 mg, 3.4 mmol, 1.0 equivalent) was dissolved in dichloromethane (5 mL) in a 250 mL Morton Flask and purged with nitrogen. The solution was then stirred and cooled in an ice-bath at 0° C. before slowly adding trifluoroacetic anhydride (1.19 mL, 8.5 mmol, 2.5 eq) via syringe. After 5 minutes of stirring the conversion to the Pummerer product was found to be complete by $^{13}$C NMR by taking an aliquot from the reaction mixture and monitoring the disappearance of phenylsulfinyl [$^{13}$C]methane ($\delta$=44 ppm) and subsequent appearance of the desired phenylthio trifluoroacetyl [$^{13}$C]methane ($\delta$=73 ppm). The reaction mixture was then allowed to reach room temperature before evaporating solvent using an increased nitrogen flow. Resulting oil was then added water (27 mL) and the heterogeneous mixture was stirred for a total of 8 days with a total of 14.5 hours of heating at 30° C. and of 7 hours of heating at 68° C. before it was hydrolyzed. The hydrolysis of the trifluoroacetate compound was found to be complete by $^{13}$C NMR by taking an aliquot from the reaction mixture and monitoring the disappearance of phenylthio trifluoroacetyl [$^{13}$C]methane ($\delta$=73 ppm) and subsequent appearance of the desired aqueous [$^{13}$C]formaldehyde ($\delta$=88 ppm). This solution was washed with dichloromethane (10 mL, 3×) to remove impurities. Diethyl phenylsulfonyl [$^{13}$C]methyl phosphonate (1.0 g, 3.4 mmol, 1.0 eq) was dissolved in DMSO (5 mL) and H$_2$O (2.5 mL) in a 250 mL Morton Flask. The mostly homogeneous mixture was stirred and cooled in an ice-bath at 0° C. An aqueous (3.5 mL) solution of K$_2$CO$_3$ (2.41 g, 17.0 mmol, 5.0 eq) was then added slowly to the reaction mixture to enable anion formation. After 10 minutes of stirring, the aqueous [$^{13}$C]formaldehyde solution (27.0 mL, 3.4 mmol, 1.0 eq) was added before the reaction was removed from the ice bath and allowed to reach room temperature. One hour after aldehyde addition the reaction was found to be complete by $^{13}$C NMR by taking an aliquot from the reaction mixture and monitoring the disappearance of diethyl phenylsulfonyl [$^{13}$C]methyl phosphonate ($\delta$=51, 53 ppm) and subsequent appearance of the desired phenyl [1,2-$^{13}C_2$]vinyl sulfone (δ=130, 131, 136, 137 ppm). The reaction mixture was then worked up by adding dichloromethane (50 mL) and organic layer was partitioned out and washed with more water (15 mL, 2×). Organic layer was then dried over sodium sulfate, filtered, and evaporated via vacuum using a rotary evaporator to yield a colorless oil (499 mg, 86% crude). Crude product contained desired product, DMSO, $^{31}$PNMR signals, and peaks which may be indicative of addition to vinyl system.

The spectra data are as follows:

$^1$H NMR (CDCl$_3$, 300 MHz): δ=5.97-6.11 (m, 1H, J=9.29 Hz), 6.32-6.51 (m, 1H), 6.32-7.01 (m, 1H), 7.53-7.92 (m, 5H$_{arom}$).

$^{13}$C NMR (CDCl$_3$, 75 MHz): δ127.45 (CH$_2$), 128.00, 129.49, 133.82, 139.57 (C$_{arom}$), 138.53 ($^{13}$CH).

The invention claimed is:
1. A mixture of a labeled compound having the structure:

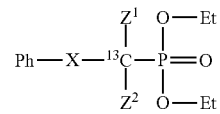

wherein Ph represents a phenyl;
wherein $Z^1$ is $^2$H;
wherein $Z^2$ is selected from the group consisting of H and $^2$H;
wherein —X is —S—; and
wherein the mixture is isotopically enriched.

* * * * *